United States Patent [19]

Hall et al.

[11] 4,022,521
[45] May 10, 1977

[54] MICROSCOPE SLIDE

[75] Inventors: Raymond V. Hall; Larry J. Harmsen, both of Edina; Robert E. Isleifson, Minneapolis, all of Minn.

[73] Assignee: Honeywell Inc., Minneapolis, Minn.

[22] Filed: Feb. 19, 1974

[21] Appl. No.: 443,661

[52] U.S. Cl. .................................. 350/95; 350/92; 356/244

[51] Int. Cl.² ........................................ G02B 21/34

[58] Field of Search ............................. 350/92–95; 356/244, 246

[56] References Cited

UNITED STATES PATENTS

| | | | |
|---|---|---|---|
| 3,198,064 | 8/1965 | Moore | 356/244 |
| 3,447,863 | 6/1969 | Patterson | 350/95 X |
| 3,510,194 | 5/1970 | Connelly | 350/95 |
| 3,742,600 | 7/1973 | Lowell | 350/95 X |
| 3,777,283 | 12/1973 | Elkins | 350/95 X |

*Primary Examiner*—David H. Rubin
*Attorney, Agent, or Firm*—Charles G. Mersereau

[57] ABSTRACT

A molded transparent plastic specimen slide for use in the microscopic examination of biological samples such as blood includes a molded slide having a pattern of micronsize projections extending from the surface which support a glass cover plate in spaced parallel relation to the slide to thereby precisely control the specimen thickness and facilitate the examination of uniform, extremely thin samples. The slide is molded of an optically clear, readily wettable rigid plastic material such as an acrylic resin. The optical clarity of the slide and cover plate materials coupled with the extremely thin cover plate and sample layer enables accurate viewing of the sample specimen on any interference phase contrast or bright field microscope.

12 Claims, 4 Drawing Figures

MICROSCOPE SLIDE

BACKGROUND OF THE INVENTION

1. Field of the invention

This invention relates to transparent specimen slides for use in microscopic examination of biological samples and, more particularly, to a microscope slide having precision projections for accurate control of specimen thickness.

2. Description of the Prior Art

In the prior art various attempts have been made to control the placement and thickness of biological samples such as blood on a microscope object slide. These include providing a recessed sample chamber in the slide, providing one or more grooves in the slide for containing the sample preparation and providing a recess in the cover plate. One such technique is illustrated and described in a British Pat. No. 679,791 to Knowles, dated Sept. 24, 1952 in which a spiral microgroove is provided in the surface of the microscope object slide to contain a fluid sample preparation such as diluted blood in a manner which causes the blood cells to line up along the spiral groove in a single layer for subsequent scanning. A cover plate is applied over the grooved microscope object slide so that the depth of the grooves will define the thickness of the fluid sample to be examined.

None of the known prior art efforts to produce a microscope object slide for the examination of a fluid biological sample with a precise sample thickness in the micron dimensional range, however, have been able to overcome drawback associated with the surface tension in the fluid sample. When the cover plate is applied to a slide of any prior art embodiments, the surface tension in the fluid sample prevents all of the excess sample from being squeezed from between the cover plate and the slide base and prevents an accurately spaced parallel fit between the cover plate and the slide base. Thus, the cover plate tends to ride on the fluid of the sample rather than on the portions of the base slide which define the parameters of the particular sample-containing cavity involved.

SUMMARY OF THE INVENTION

According to the present invention, the problems associated with accurately controlling the thickness of a fluid biological sample on a microscope object slide is solved by the provision of a special slide and cover plate. The slide is provided with a pattern of micron-size projections extending from its surface which precisely control the specimen thickness allowing a controlled, extremely thin sample layer and also supporting the cover plate spaced parallel in relation to the slide. The micron-size projections are, in the preferred embodiment, molded integral with the microscope object slide and take up only a small fraction of the total slide area theby allowing the fluid to be readily dispersed in all directions therebetween. Typically, in the case of a blood sample, the projections are from about 15 microns to about 25 microns in diameter at the top and from about 0.1 micron to 15 microns in height and located on the sample portion of the slide in a pattern on centers from about 200 microns to about 1,000 microns apart. Along one or more edges of the pattern, in the preferred embodiment, the projections are spaced closer together, normally from about 20 microns to about 100 microns apart, in order for the precise height of the projections to be more readily checked by a proficorder or other microtopographical measuring device during manufacture to assure uniformity.

The optical slides are normally molded from plastic molding compounds which produce slides with excellent optical clarity and are easily wetted by an aqueous solution. The preferred materials include acrylic resins, styrene and styrene copolymers. Other materials include ionomer compounds and methylpentane polymers. While the cover plates may be made of similar material, they are normally made of glass.

The same is applied to the slide base in an amount somewhat less than the inter-projection volume. This "sub-critical" volume yields a concave meniscus about the periphery of the portion containing the projections when the cover plate is applied and the resulting internal capillarity pulls and holds the cover plate against the projections. This assures that the cover plate will rest on the pattern of projections rather than on the fluid therebetween. Thus, the preparation of a fluid biological sample of a precise controlled thickness as, for example, a sample of blood one monolayer of blood cells thick is possible.

DESCRIPTION OF THE PREFERRED EMBODIMENT

Figure 1:
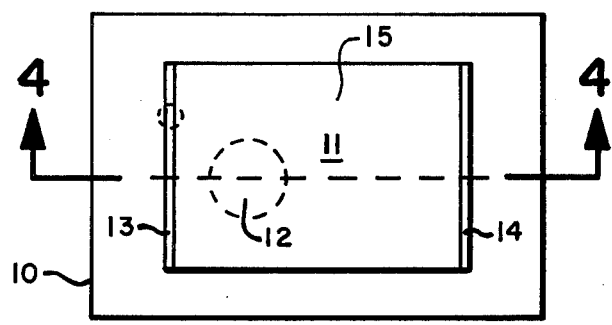
FIG. 1 is a top view of the microscope object slide of the invention.

FIG. 1 discloses the generally rectangular microscope slide 10 of the invention which may be of any size convenient for the particular application of the slide. Within the confines of the slide 10 is a second area 11 which is defined by a pattern of microscopic protrusions 12. The area 11 is shown as a rectangular pattern in the preferred embodiment but may take any shape desired for the particular analysis required.

Figure 2:
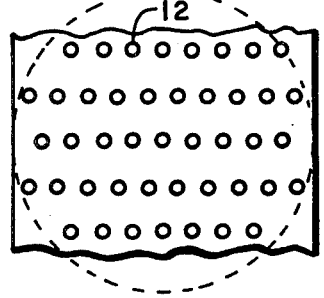
FIG. 2 is an enlarged view of the edge pattern of projections circled in FIG. 1.
Figure 3:
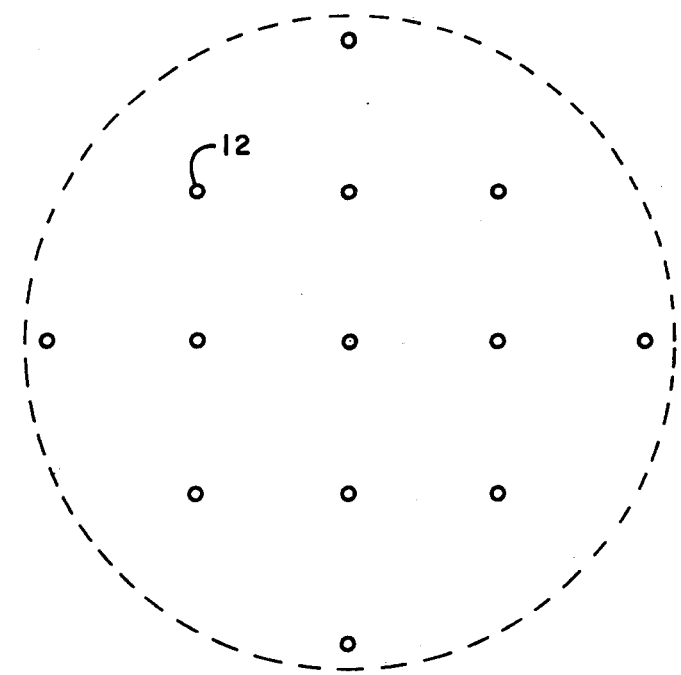
FIG. 3 is an enlarged view of the central projection pattern circled in FIG. 1.

As can more readily be seen in the enlarged views of FIGS. 2 and 3 the pattern of the microscopic projections 12 along edges 13 and 14 of area 11 are much more closely spaced than those in the central portion 15. This closer spacing is utilized along one or more sides to facilitate quality control checking of the height of the projection pattern. Checking is normally accomplished by a proficorder device which is utilized to measure micron-size differences in surface topographies automatically. Thus, with the closer spacing along one or more edges the ability of the microscopic sensing point of the proficorder device to strike and measure one or more of the projections is greatly increased. Typically, the projections in the central area 15 are round posts, squares or rectangles having a nomimal diameter of from approximately 15 microns to approximately 25 microns and are located in a regular pattern with centers approximately 200 to 1,000 microns apart. In the more densely packed edge portions ot the pattern 13 and 14, the projections are the same size as those in the central portion of the pattern, however, the projections are typically spaced with centers about 100 to 150 microns apart in the direction along either the edge 13 or 14 and from about 25 to 50 microns apart in the direction perpendicular to these edges.

From the above dimensions it can readily be seen that the pattern of projections is extremely open in all directions to greatly facilitate the escape of any excess sample between the projections. The general pattern of FIG. 3 is typically 95 percent open and that of FIG. 2 approximately 85 percent open in the direction extending away from the center of the slide 10.

The projections may be any height required for the specimen thickness desired. Typically, in the case of the analysis of blood cells, the projections are about 2 to 3 microns in height to allow a uniform single layer of blood cells in the specimen. The large amount of open area in relation to the area occupied by the projections overcomes problems associated with the dispersion of the sample within the area 11.

Figure 4:
FIG. 4 is a sectional view taken substantially along line 4—4 of FIG. 1 with the cover plate added.

It should also be noted that although the projections have been described as round posts, they may be in any desired configuration. Higher projections may be larger at the base than at the top. The top area, however, must be small enough so that sample liquid and biological cells do not collect there to interfere with the precise allignment of the cover plate 16 (FIG. 4). All of the projections 12 should be of the same dimensional configuration so that the projections checked along the edges 13 and 14 are representative of all the projections on the slide 10.

The preferred sample volume is one which does not exceed the volume defined by the inter-projection area times the height of the projections 12. A sample volume of less that the above defined volume limit is known as a sub-critical volume. With a sample of a sub-critical volume, the subsequent application of the cover plate 16 produces a concave meniscus between the cover plate 16 and the slide base 10 about the periphery of the area 11. In the same fashion, the internal capillary action of the sample liquid between the projections exerts an inward pull between the cover plate and the slide base which results in a tight uniform fit at the projection-cover plate interface. This, of course, allows the precise determination of specimen layer thickness which has long been sought in the art. FIG. 4 illustrates a sectional view of the object slide 10 with cover plate 16 supported by the projections 12. If a sample of a volume larger than the critical volume is used, the excess may be removed as by swabbing about the periphery of the area 11. Once the excess is removed a tight cover plate will result.

As mentioned above, the slide is typically made of a moldable plastic material having excellent optical clarity and excellent wetting characteristics for aqueous preparations. It must also be sufficiently rigid to maintain a parallel relation between the cover plate and slide in the optical microscope slide. To enhance results the material selected should exhibit a refractive index close to that of the particular biological sample involved. That for a saline blood solution is about 1.3. One class of compounds which exhibit all the required properties are the polymers of the esters of acrylic and methylacrylic acid which upon polymerization yield acrylic or acryloid resins. In the preferred embodiment for blood analysis, a polymer of methyl methacrylate, a strong thermoplastic solid that is highly transparent and has a high refractive index, is normally used. Examples of other compounds having the requisite properties and which may also be used include polystyrene and copolymers of styrene such as acrylic-styrene, styrene-acrylonitrile (SAN), acrylonitrilebutadiene-styrene (ABS), ionomer compounds such as Surlyn A and methylpentane (TRX) polymers.

The microscope object slide of the present invention is normally produced with integral projections from a mold utilizing well-known molding techniques. The mold is normally made by photoetching techniques which are typically utilized in the production of microcircuits in the electronics industry. Thus, typically, a silicon dioxide layer is grown or deposited on a silicon wafer and thereafter a photoresist layer is applied, as by spinning, to the silicon dioxide layer. A microphoto mask containing the precise pattern of the projections to be used on the final slide is then placed on the photoresist layer. The photoresist is then developed and the pattern is etched into the silicon dioxide layer in a well-known manner. The photoresist is then removed and the etched wafer may be sawed to the desired thickness to be used as a pattern mold insert. The insert is then placed in the mold cavity and the slides molded in a well-known manner. Utilizing this technique it has been possible to manufacture slides having the typical projection pattern described above wherein uniform projections as little as 0.1 micron in height or as much as 15 microns in height are produced.

While the cover plates can be made of the same type of plastic materials as the slides, glass is preferred as the material of construction. This is principally because a glass cover plate may be made extremely thin, i.e., as thin as 0.17 mm; whereas the present limits on molding a plastic cover plate are about 0.35 mm. In some applications of the slide of the present invention as phase contrast microscopy, for example, this difference may be critical because of the very shallow depth of field of the phase contrast microscope. Slides made utilizing the above process are extremely uniform insofar as the height of the projection is concerned as quality control checks utilizing a proficorder have indicated. The slides themselves may be made as thin as 0.50 mm and the cover plates, as mentioned above, may be made as thin as 0.17 mm.

The superior optical clarity achieved by utilizing materials such as polymethylmethacrylate, other acrylics, styrenes and their copolymer combinations coupled with a glass cover plate the ability to achieve a uniform, extremely thin specimen layer along with extremely thin slide and cover plate enables the examination of a typical monolayer specimen such as that utilized for a white blood cell count with the cover plate in place on any known interference, phase contrast or bright field microscope system without any fear of any optical distortion or depth of field focusing problems.

The embodiments of the invention in which an exclusive property or right is claimed are defined as follows:

1. A specimen slide for the microscopic examination of a fluid biological sample comprising:
   a substantially flat first member having a surface provided with a plurality of integral microprojections spaced thereon in a predetermined pattern and extending a substantially equal distance therefrom, wherein said projections are spaced in a manner which allows the free flow of a fluid sample in all directions therebetween
   and a substantially flat second member having a surface adapted to be supported on said microprojections in spaced parallel relation to said surface of first member thereby precisely controlling the thickness of said sample.

2. The specimen slide of claim 1 wherein said projections extend from about 0.1 to about 15.0 microns from said surface of said first member.

3. The specimen slide of claim 2 wherein said projections are columnar in shape, each having a top diameter from about 15 microns to about 75 microns and are located on centers from about 200 microns to about 1,000 microns apart.

4. The specimen slide of claim 1 wherein a plurality of said projections along at least one edge of said pattern of projections spaced closer together than the remainder of said pattern to facilitate quality control checking of the height of said projections above said surface of said first member.

5. The specimen slide of claim 4 wherein said projections are columnar in shape, each having a diameter from about 15 microns to about 75 microns and are located on centers from about 200 microns to about 1,000 microns apart and wherein said projections along at least one edge of said pattern are the same size and shape as said central projections and are located on centers from about 20 microns to about 100 microns apart.

6. The specimen slide of claim 1 wherein said second member is glass.

7. The specimen slide of claim 1 wherein said first member is molded from a plastic molding compound selected from a class consisting of moldable, optically clear compounds which are easily wetted by aqueous biological samples.

8. The specimen slide of claim 7 wherein the thickness of said first member is from approximately 0.5 mm to approximately 2.0 mm and the thickness of said second member is from approximately 0.17 mm to approximately 0.5 mm.

9. The specimen slide of claim 7 wherein said second member is molded from a plastic molding compound from the same class as said first member.

10. The specimen slide of claim 7 wherein said first member is made of a compound selected from the group consisting of acrylic resins, styrene, acrylic-styrene copolymer, styrene-actylonitrile copolymer, acrylonitrile-butadiene-styrene copolymer, an ionomer, and methylpentane polymer.

11. The specimen slide of claim 10 wherein said first member is molded from an acrylic resin.

12. The specimen slide of claim 10 wherein said first member is molded from an acrylic-styrene copolymer.

* * * * *